US008907146B2

(12) United States Patent
Tung et al.

(10) Patent No.: US 8,907,146 B2
(45) Date of Patent: Dec. 9, 2014

(54) PROCESS FOR THE PREPARATION OF 1-CHLORO-3,3,3-TRIFLUOROPROPENE USING A PHASE TRANSFER CATALYST

(71) Applicant: Honeywell International Inc., Morristown, NJ (US)

(72) Inventors: Hsueh Sung Tung, Getzville, NY (US); Haiyou Wang, Amherst, NY (US); Daniel C. Merkel, West Seneca, NY (US); Stephen A. Cottrell, Williamsville, NY (US); Konstantin A. Pokrovski, Orchard Park, NY (US); Ian Shankland, Randolph, NJ (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 14/168,065

(22) Filed: Jan. 30, 2014

(65) Prior Publication Data

US 2014/0221704 A1 Aug. 7, 2014

Related U.S. Application Data

(60) Provisional application No. 61/760,321, filed on Feb. 4, 2013.

(51) Int. Cl.
C07C 17/20 (2006.01)
C07C 17/21 (2006.01)

(52) U.S. Cl.
CPC ............... *C07C 17/204* (2013.01); *C07C 17/21* (2013.01); *C07C 17/206* (2013.01)
USPC .......................................... 570/160

(58) Field of Classification Search
CPC ............................. C07C 17/206; C07C 17/21
USPC ........................................... 570/160
See application file for complete search history.

(56) References Cited

U.S. PATENT DOCUMENTS

| | | |
|---|---|---|
| 4,140,719 A | 2/1979 | Tull et al. |
| 5,710,352 A | 1/1998 | Tung |
| 6,403,847 B1 | 6/2002 | Nakada et al. |
| 6,844,475 B1 | 1/2005 | Tung et al. |
| 8,373,010 B2 | 2/2013 | Merkel et al. |
| 2010/0237279 A1 | 9/2010 | Hulse et al. |
| 2011/0201853 A1 | 8/2011 | Tung et al. |
| 2012/0059201 A1 | 3/2012 | Merkel et al. |
| 2013/0211156 A1 | 8/2013 | Nair et al. |

OTHER PUBLICATIONS

PCT Search Report and Written Opinion—PCT/US2014/014360—May 2, 2014.

*Primary Examiner* — Elvis O Price
(74) *Attorney, Agent, or Firm* — Bruce O. Bradford

(57) ABSTRACT

Disclosed is a process in which the fluorination of an organic reactant comprising 1,1,1,3,3-pentachloropropane (240fa) with anhydrous HF is conducted in the presence of an effective amount of a phase-transfer catalyst which facilitates the reaction between these incompatible reaction components to produce 1-chloro-3,3,3-trifluoro-propene (1233zd). Other organic reactant materials include 1,1,3,3-tetrachloropropene (HCO-1230za), 1,3,3,3-tetrachloropropene (HCO-1230zd), and various mixtures with or without 240fa.

27 Claims, No Drawings

PROCESS FOR THE PREPARATION OF 1-CHLORO-3,3,3-TRIFLUOROPROPENE USING A PHASE TRANSFER CATALYST

CROSS-REFERENCE TO RELATED APPLICATION

This application claims benefit of U.S. Provisional Patent Application Ser. No. 61/760,321 filed Feb. 4, 2013, the disclosure of which is hereby incorporated herein by reference.

FIELD OF THE INVENTION

This invention relates to a process for preparing halogenated organic compounds, more particularly to a process for preparing hydrochlorofluoroolefins, and even more particularly to a process for producing 1-chloro-3,3,3-trifluoropropene (HCFO-1233zd) from 1,1,1,3,3-pentachloropropane (HFC-240fa) by the use of a phase transfer catalyst.

BACKGROUND OF THE INVENTION

Chlorofluorocarbon (CFC) based chemicals have been widely used in industry in a variety of different applications including as refrigerants, aerosol propellants, blowing agents and solvents, among others. However, certain CFCs are suspected of depleting the Earth's ozone layer. Accordingly, more environmentally friendly substitutes have been introduced as replacements for CFCs. For example, 1,1,1,3,3-pentafluoropropane (HFC-245fa) is recognized as having favorable physical properties for certain industrial applications, such as foam blowing agents and solvents, and therefore is considered to be a good substitute for the CFCs previously used for these applications. Unfortunately, the use of certain hydrofluorocarbons, including HFC-245fa, in industrial applications is now believed to contribute to the global warming. Accordingly, more environmentally friendly substitutes for hydrofluorocarbons are now being sought.

The compound 1-chloro-3,3,3-trifluoropropene, also known as HCFO-1233zd or simply 1233zd, is a candidate for replacing HFC-245fa in some applications, including uses as blowing agents and solvents. 1233zd has a Z-isomer and an E-isomer. Due to differences in the physical properties between these two isomers, pure 1233zd(E), pure 1233zd(Z), or certain mixtures of the two isomers may be suitable for particular applications as refrigerants, propellants, blowing agents, solvents, or for other uses.

It is known that 1-chloro-3,3,3-trifluoropropene can be prepared through the fluorination of 1,1,1,3,3-pentachloropropane (HCC-240fa) in a liquid phase reactor. The uncatalyzed HCC-240fa fluorination using anhydrous HF is slow due to their low solubility and limited contact surface area between HCC-240fa and HF.

Also known are methods to improve the reaction rate and/or to elevate the conversion of HCC-240fa to 1233zd. These include an increase in the agitation speed and/or increase the reaction temperature. However, the increase in agitation speed can increase the contact surface area between two phases only to a certain degree. Thus, the reaction rate or the conversion is limited by the increase in the agitation speed. While it is true that the rate of a reaction is increased with increasing temperature, by-products are accompanied by elevating the solution temperature. Hence, there is a need for means by which the reaction rate can be improved without these detrimental impacts.

SUMMARY OF THE INVENTION

In one embodiment, the present invention is directed to a process in which the fluorination of 240fa with anhydrous HF is conducted in the presence of a phase-transfer catalyst, which facilitates the reaction between these two incompatible reaction components to produce 1-chloro-3,3,3-trifluoropropene.

In another embodiment, the process of the present invention involves a single-step fluorination reaction of an organic reactant comprising 1,1,1,3,3-pentachloropropane (HCC-240fa) with anhydrous HF in the presence of a phase-transfer catalyst and optionally in the presence of a polar aprotic solvent to produce 1-chloro-3,3,3-trifluoro-propene (1233zd) plus HCl as a by-product. In addition to HCC-240fa as the organic reactant material, the 240fa can be in a mixture with one or more of 1,1,3,3-tetra-chloropropene (HCO-1230za) and/or 1,3,3,3-tetrachloropropene (HCO-1230zd). Alternatively, each of 1230za and/or 1230zd can be the primary organic reactant material, which can optionally be in a mixture with 240fa and/or the other of 1230zd or 1230za.

It should be appreciated by those persons having ordinary skill in the art(s) to which the present invention relates that any of the features described herein in respect of any particular aspect and/or embodiment of the present invention can be combined with one or more of any of the other features of any other aspects and/or embodiments of the present invention described herein, with modifications as appropriate to ensure compatibility of the combinations. Such combinations are considered to be part of the present invention contemplated by this disclosure.

It is to be understood that both the foregoing general description and the following detailed description are exemplary and explanatory only and are not restrictive of the invention as claimed. Other embodiments will be apparent to those skilled in the art from consideration of the specification and practice of the invention disclosed herein.

DETAILED DESCRIPTION OF THE INVENTION

As set forth above, the present invention is directed to a process in which the fluorination of an organic material comprising 240fa with anhydrous HF is conducted in the presence of a phase-transfer catalyst, which facilitates the reaction between these two incompatible reaction components.

In one embodiment, the reaction chemistry for this process of the present invention involves a single-step fluorination reaction of an organic reactant comprising 1,1,1,3,3-pentachloropropane (HCC-240fa), 1,1,3,3-tetra-chloropropene (HCO-1230za), 1,3,3,3-tetrachloropropene (HCO-1230zd), or their various mixtures, with anhydrous HF in the presence of a phase-transfer catalyst and optionally in the presence of a polar aprotic solvent to produce 1-chloro-3,3,3-trifluoro-propene (1233zd) plus HCl as a by-product. A preferred organic reactant material comprises 240fa.

The fluorination reaction is conveniently and preferably conducted in the presence of a phase transfer catalyst. The phase transfer catalyst facilitates the reaction of these dissimilar and incompatible components, namely selected organic reactants and HF. While various phase transfer catalysts may function in different ways, their mechanism of action is not determinative of their utility in the present invention provided that the phase transfer catalyst facilitates the fluorination reaction.

One useful phase-transfer catalyst comprises an onium salt which includes quaternary phosphonium salt and quaternary ammonium salt. Examples of such compounds include, but are not limited to, tetramethylammonium chloride, tetramethylammonium bromide, benzyltriethylammonium chloride, methyltrioctylammonium chloride (available commercially under the brands Aliquat 336 and Adogen 464), tetran-butylammonium chloride, tetra-n-butylammonium bromide, tetra-n-butylammonium hydrogen sulfate, tetra-n-butyl-phosphonium chloride, tetraphenylphosphonium bromide, tetraphenylphosphonium chloride, triphenylmethylphosphonium bromide, triphenylmethylphosphonium chloride, 4-dialkylaminopyridinium salts such as tetraphenylarsonium chloride, bis[tris(dimethyl-amino)phosphine]iminium chloride and tetratris-[tris(dimethylamino)phosphinimino]-phosphonium chloride. One preferred, but non-limiting example of a phase transfer catalyst is Aliquat 336.

An effective amount of the phase transfer catalyst should be used in order to effect the desired reaction; such an amount can readily be determined by limited experimentation once the reactants, process conditions and phase transfer catalyst are selected. Typically, the amount of catalyst used relative to the amount of selected reactants is from about 0.001 to about 10 mol %; preferably, from about 0.01 to about 5 mol %; and even more preferably, from about 0.05 to about 5 mol %.

The fluorination reaction can be optionally carried out in the presence of a polar aprotic solvent for better results in addition to the presence of a phase transfer catalyst. Non-limiting examples of polar aprotic solvent include dimethylformamide, dimethyl sulfoxide, and the like. An effective amount of solvent should be used in order to effect the desired reaction; such an amount can be determined by limited experimentation once the reactants, process conditions and phase transfer catalyst are selected. Typically, the amount of solvent used relative to the amount of selected reactant is from about 0.001 to about 10 mol %; preferably, from about 0.01 to about 5 mol %; and even more preferably, from about 0.05 to about 5 mol %.

The fluorination reaction of HCC-240fa, HCO-1230za, HCO-1230zd, or their various mixtures, can be carried out in a in a liquid-phase, agitated reactor. Preferably the reactor is constructed from materials which are resistant to the corrosive effects of the HF and HCl, such as Hastelloy-C, Inconel, Monel, Incalloy, or fluoropolymer-lined steel vessels. The reactor is equipped with an agitator. Such liquid-phase fluorination reactors are well known in the art.

In preferred embodiments, the reactor is further equipped with a rectifying column which permits the desired product to leave (along with by-product HCl, light organics such as 1,3,3,3-tetrafluoropropene (HFO-1234ze), and hydrogen fluoride in the amount greater than that in azeotropic composition), while retaining the bulk of the HF, plus under-fluorinated organics such as 1,1,3,3-tetrachloro-1-fluoropropane (HCFC-241fa), 1,3,3-trichloro-3-fluoropropene (HCFO-1231zd), 1,3,3-trichloro-1,1-difluoro-propane (HCFC-242fa), 1,3-dichloro-3,3-difluoropropene (HCFO-1232zd), 1,1-dichloro-3,3,3-trifluoropropane (HCFC-243fa), and the like.

HF, organic feed, namely, HCC-240fa, or HCO-1230za, or HCO-1230zd, or their various mixtures, a phase transfer catalyst, and optionally a polar aprotic solvent can be charged to the fluorination reactor and the reaction can be initiated immediately upon heating to the desired reaction temperature while maintaining agitation. The flow of HF to the reactor can be resumed, and addition of the selected reactant can be started immediately to cause continuous reaction.

Alternatively, a large amount of HCC-240fa, or HCO-1230za, or HCO-1230zd, or their various mixtures can be added at one time as a batch charge, and then HF can be added gradually to the reactor (a semi-batch operation). Alternatively, a large amount of HF can be added at one time as a batch charge, and then HCC-240fa, or HCO-1230za, or HCO-1230zd, or their various mixtures can be added gradually to the reactor (a semi-batch operation).

Proper temperature control of the coolant and sufficient reflux action are desirable for optimum operation of the rectifying column to be effective. General operating conditions which have been found to work well for the reaction and rectifying column are: reactor operating pressure of 100 psig to 500 psig maintained by a control valve on the exiting flow from the rectifying column; reactor temperature of 65° C. to 175° C., with heat primarily supplied by steam flow into the reactor jacket, additionally provided by superheating the HF feed to 70° C. to 180° C. with high-pressure steam; application of −40° C. to 35° C. cooling to the heat exchanger on top of the rectifying column to induce reflux; temperature in the center portion of the stripper about 5° C. to 60° C. below that in the reactor.

Preferably, the reaction is maintained under conditions of temperature and/or pressure effective to increase the relative ratio of (E) to (Z) isomers of 1233zd while also minimizing the reaction of HF with the resulting 1233zd which would lead to the formation of HFC-244fa, which in turn can react further to produce HFO-1234ze. It has been discovered that maintaining the reaction under the following operating conditions, particularly, a temperature range of 65° C. to 175° C., more preferably 85° C. to 155° C., and most preferably 95° C. to 150° C., produces a high ratio of 1233zd(E) to 1233zd(Z).

The following are examples of the invention and are not to be construed as limiting.

COMPARATIVE EXAMPLES

Example 1

In this batchwise experiment, no phase-transfer catalyst was used. 282.9 grams of HF and 246.2 grams of HCC-240fa (1,1,1,3,3-pentachloropropane) (12.4 to 1 mole ratio HF:HCC-240fa) were charged to a one gallon agitated Parr reactor at room temperature. The mixer was then turned on ensuring the reactor contents were well mixed. Then the reactor was heated to the desired temperature. Upon heating the pressure began to rise as HCl by-product was produced as a result of a fluorination reaction. The reactor was heated to about 110° C. over several hours and held at that temperature. The pressure was controlled in the range of 250 psig to 325 psig by venting off the HCl generated in the reaction to a dry-ice trap (DIT).

At the completion of the reaction, i.e., after about 9.5 hrs., (as determined by a lack of HCl generation), the pressure from the reactor was vented into the DIT. The crude product from the DIT was transferred into a 1 L Monel absorption cylinder (frozen in dry-ice) with about 400 grams of water. The absorption cylinder was allowed to warm up to room temperature and a sample of an organic layer that had formed in the cylinder (aqueous and organic layers were present in the cylinder upon discharge) was taken and analyzed by gas chromatography (GC). GC results showed 4.48 GC % 245fa, 90.61 GC % 1233zd(E), 0.22 GC % 244fa, 2.93 GC % 1233zd(Z).

The amount of organic collected was later quantified by further analysis of the different phases and amounted to 75.4 grams. The organic remaining in the reactor after venting was recovered by quenching the reactor with about 300 to 400 grams of water to absorb HF and HCl, and then adding about 100 grams of carbon tetrachloride. The reactor was then opened and its contents discharged into a plastic bottle. The organic was separated from the aqueous phase by use of a reparatory funnel. The amount of heavies collected from the reactor was calculated by subtracting the weight of $CCl_4$ added to the reactor from the total weight of organic phase collected and amounted to 96.9 grams. GC/MS and GC analysis of the organic layer followed and revealed 3 distinct peaks attributed to under-fluorinated species HCFC-241fa, 91.057 GC %, HCFC-242fa, 0.760 GC %, and the starting material HCC-240fa, 8.183 GC %.

Example 2

The experiment described in Example 1 is repeated using the same equipment and procedure except for the use of a phase-transfer catalyst. 2 g of Aliquat 336 (one of many similarly reactive commercially available quaternary type phase transfer catalysts) is also charged into the reactor. The reactor is heated to 110° C. and held at that temperature. It is found that within 5 hours, the reaction is completed. About 80 g of light organics is recovered as crude product; GC results show the organics contain 3.48 GC % 245fa, 91.61 GC % 1233zd(E), 0.12 GC % 244fa, 3.03 GC % 1233zd(Z). About 90 g of heavy organics is recovered from the reactor; GC analysis indicates the organics comprise under-fluorinated species HCFC-241fa, 90.03 GC %, HCFC-242fa, 2.48 GC %, and the starting material HCC-240fa, 6.50 GC %.

As used herein, the singular forms "a", "an" and "the" include plural unless the context clearly dictates otherwise. Moreover, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A process to produce 1-chloro-3,3,3-trifluoropropene (1233zd) comprising the fluorination of an organic reactant comprising 1,1,1,3,3-pentachloropropane (240fa) with anhydrous hydrogen fluoride (HF) in the presence of an effective amount of a phase-transfer catalyst.

2. The process of claim 1, wherein the 240fa is in a mixture with 1,1,3,3-tetrachloropropene (HCO-1230za).

3. The process of claim 1, wherein the 240fa is in a mixture with 1,3,3,3-tetrachloropropene (HCO-1230zd).

4. The process of claim 1, wherein the 240fa is in a mixture with both 1,1,3,3-tetrachloropropene (HCO-1230za) and 1,3,3,3-tetrachloropropene (HCO-1230zd).

5. The process of claim 1, wherein the phase-transfer catalyst comprises an onium salt.

6. The process of claim 5, wherein the onium salt comprises a quaternary phosphonium salt.

7. The process of claim 6, wherein quaternary phosphonium salt is selected from the group consisting of tetra-n-butyl-phosphonium chloride, tetraphenylphosphonium bromide, tetraphenylphosphonium chloride, triphenylmethylphosphonium bromide, and triphenylmethylphosphonium chloride.

8. The process of claim 5, wherein the onium salt comprises a quaternary ammonium salt.

9. The process of claim 8, wherein the quaternary ammonium salt is selected from the group consisting of tetramethylammonium chloride, tetramethylammonium bromide, benzyltriethylammonium chloride, methyltrioctylammonium chloride, tetra-n-butylammonium chloride, tetra-n-butylammonium bromide, and tetra-n-butylammonium hydrogen sulfate.

10. The process of claim 1, wherein the effective amount of the phase-transfer catalyst used relative to the amount of the organic reactant is from about 0.001 to about 10 mol %.

11. The process of claim 1, wherein the effective amount of the phase-transfer catalyst used relative to the amount of the organic reactant is from about 0.01 to about 5 mol %.

12. The process of claim 1, wherein the effective amount of the phase-transfer catalyst used relative to the amount of the organic reactant is from about 0.05 to about 5 mol %.

13. A process to produce 1-chloro-3,3,3-trifluoropropene (1233zd) comprising the fluorination of an organic reactant comprising 1,1,3,3-tetrachloropropene (HCO-1230za) with anhydrous hydrogen fluoride (HF) in the presence of an effective amount of a phase-transfer catalyst.

14. The process of claim 13, wherein the 1230za is in a mixture with 1,1,1,3,3-pentachloropropane (240fa).

15. The process of claim 13, wherein the 1230za is in a mixture with 1,3,3,3-tetrachloropropene (HCO-1230zd).

16. The process of claim 13, wherein the 1230za is in a mixture with both 1,1,1,3,3-pentachloropropane (240fa) and 1,3,3,3-tetrachloropropene (HCO-1230zd).

17. A process to produce 1-chloro-3,3,3-trifluoropropene (1233zd) comprising the fluorination of an organic reactant comprising 1,3,3,3-tetrachloropropene (HCO-1230zd) with anhydrous hydrogen fluoride (HF) in the presence of an effective amount of a phase-transfer catalyst.

18. The process of claim 17, wherein the 1230zd is in a mixture with 1,1,1,3,3-pentachloropropane (240fa).

19. The process of claim 17, wherein the 1230zd is in a mixture with 1,1,3,3-tetrachloropropene (HCO-1230za).

20. The process of claim 17, wherein the 1230zd is in a mixture with both 1,1,1,3,3-pentachloropropane (240fa) and 1,1,3,3-tetrachloropropene (HCO-1230za).

21. The process of claim 1, wherein the fluorination reaction is conducted in the presence of a polar aprotic solvent.

22. The process of claim 21, wherein polar aprotic solvent is selected from the group consisting of dimethylformamide, and dimethyl sulfoxide.

23. The process of claim 21, wherein an effective amount of the polar aprotic is used, relative to the amount of organic reactant.

24. The process of claim 23, wherein the amount of solvent used relative to the amount of organic reactant is from about 0.001 to about 10 mol %.

25. The process of claim 23, wherein the amount of solvent used relative to the amount of organic reactant is from about 0.01 to about 5 mol %.

26. The process of claim 23, wherein the amount of solvent used relative to the amount of organic reactant is from about 0.05 to about 5 mol %.

27. The process of claim 1, wherein the phase-transfer catalyst is selected from the group consisting of 4-dialkylaminopyridinium salts, tetraphenylarsonium chloride, bis[tris(dimethyl-amino)phosphine]iminium chloride, and tetratris[tris(dimethylamino)phosphinimino]phosphonium chloride.

* * * * *